(12) United States Patent
Steiner et al.

(10) Patent No.: US 8,614,164 B2
(45) Date of Patent: Dec. 24, 2013

(54) IRON- AND COPPER-COMPRISING HETEROGENEOUS CATALYST AND PROCESS FOR PREPARING OLEFINS BY REACTING CARBON MONOXIDE WITH HYDROGEN

(75) Inventors: Jochen Steiner, Bensheim (DE); Kerem Bay, Ludwigshafen (DE); Vera Werner, Lingenfeld (DE); Jürgen Amann, Dudenhofen (DE); Stefan Bunzel, Altrip (DE); Claudia Moßbacher, Deidesheim (DE); Joachim Müller, Grünstadt (DE); Ekkehard Schwab, Neustadt (DE); Markus Weber, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 280 days.

(21) Appl. No.: 12/939,281

(22) Filed: Nov. 4, 2010

(65) Prior Publication Data

US 2011/0112203 A1 May 12, 2011

(30) Foreign Application Priority Data

Nov. 6, 2009 (EP) .................................... 09175224

(51) Int. Cl.
| | |
|---|---|
| *B01J 23/58* | (2006.01) |
| *C07C 27/00* | (2006.01) |
| *B01J 23/70* | (2006.01) |
| *B01J 23/72* | (2006.01) |
| *B01J 23/74* | (2006.01) |

(52) U.S. Cl.
USPC ........... 502/330; 502/331; 502/338; 502/524; 518/700; 518/713; 518/715; 518/719; 518/721

(58) Field of Classification Search
USPC .......... 502/330, 331, 338, 524; 518/700, 713, 518/715, 719, 721
See application file for complete search history.

(56) References Cited

U.S. PATENT DOCUMENTS

| | | | |
|---|---|---|---|
| 2,417,164 A | 3/1947 | Huber, Jr. | |
| 3,397,057 A * | 8/1968 | Harrington et al. | ............. 419/31 |

(Continued)

FOREIGN PATENT DOCUMENTS

| | | |
|---|---|---|
| DE | 528463 C | 6/1931 |
| DE | 2507647 A1 | 9/1976 |

(Continued)

OTHER PUBLICATIONS

DIN 66 133—Jun. 1993.

(Continued)

*Primary Examiner* — Patricia L Hailey
(74) *Attorney, Agent, or Firm* — Novak Druce Connolly Bove + Quigg LLP

(57) ABSTRACT

Iron- and copper-containing heterogeneous catalyst, and a process for producing it, including the following steps: thermal decomposition of gaseous iron pentacarbonyl to give carbonyl iron powder having spherical primary particles; treatment of carbonyl iron powder with hydrogen, resulting in the metallic spherical primary particles at least partly agglomerating; surface oxidation of the iron particles to form iron oxide; contacting the particles with an aqueous solution of a copper compound; drying in the presence of oxygen and subsequent calcination in the absence of oxygen, resulting in oxygen-comprising copper compounds on the particles; and finally reaction of these with the iron oxide to form a mixed oxide of the formula $Cu_xFe_{3-x}O_4$, where $0<x\leq1$. Process for preparing olefins by reacting carbon monoxide with hydrogen in the presence of a catalyst, wherein the abovementioned iron- and copper-comprising heterogeneous catalyst is used as catalyst.

25 Claims, 7 Drawing Sheets

(56) References Cited

U.S. PATENT DOCUMENTS

| | | | |
|---|---|---|---|
| 3,994,734 A * | 11/1976 | Cuthbert | 106/1.23 |
| 4,459,369 A * | 7/1984 | Passariello | 502/306 |
| 4,544,674 A | 10/1985 | Fiato et al. | |
| 4,604,375 A * | 8/1986 | Soled et al. | 502/241 |
| 4,618,597 A * | 10/1986 | Fiato et al. | 502/324 |
| 4,833,040 A * | 5/1989 | Fishman et al. | 428/570 |
| 5,100,856 A | 3/1992 | Soled et al. | |
| 5,118,715 A | 6/1992 | Iglesia et al. | |
| 5,169,538 A * | 12/1992 | Habermann et al. | 210/709 |
| 5,248,701 A | 9/1993 | Soled et al. | |
| 2004/0127582 A1 | 7/2004 | Kiss et al. | |
| 2009/0005464 A1 | 1/2009 | Hoffer et al. | |

FOREIGN PATENT DOCUMENTS

| | | |
|---|---|---|
| DE | 2822656 A1 | 12/1978 |
| DE | 2919921 A1 | 11/1980 |
| GB | 2050859 A | 1/1981 |
| WO | WO-2007/060186 A1 | 5/2007 |
| WO | WO-2009/013174 A2 | 1/2009 |
| WO | WO 2009/071463 | 6/2009 |
| WO | WO 2010/028995 | 3/2010 |
| WO | WO 2011/054734 | 3/2011 |
| WO | WO 2011/054735 | 3/2011 |
| WO | WO 2011/054738 | 3/2011 |

OTHER PUBLICATIONS

DIN ISO 9277—May 2003.
U.S. Appl. No. 13/063,321, filed Mar. 10, 2011, Steiner et al.
U.S. Appl. No. 12/950,646, filed Nov. 19, 2010, Steiner et al.
U.S. Appl. No. 12/939,903, filed Nov. 4, 2010, Steiner et al.
U.S. Appl. No. 12/940,772, filed Nov. 5, 2010, Steiner et al.
International Search Report, PCT/EP2010/066383—Oct. 28, 2010, Feb. 23, 2011.
V. P. Klevtsova et al., The Synthesis of Hydrocarbons and Oxygen-Containing Compounds From Carbon Monoxide and Hydrogen Over Iron-Copper Catalysts, Chemistry and Technology of Fuels and Oils, Bd. 1, Nr. 6, Jun. 1964, pp. 424-429.
G. Pourroy et al., Synthesis of $Cu°/Cu(II)$ substituted magnetite nanocomposites in aqueous media, Journal of Alloys and Compounds, 2001, pp. 267-269.
English translation, International Preliminary Report on Patentability, PCT/EP2010/066382.

* cited by examiner

IRON- AND COPPER-COMPRISING HETEROGENEOUS CATALYST AND PROCESS FOR PREPARING OLEFINS BY REACTING CARBON MONOXIDE WITH HYDROGEN

CROSS-REFERENCE TO RELATED APPLICATIONS

This application claims benefit of European patent application no. 09175224.6 filed Nov. 6, 2009, the contents of which are incorporated herein by reference in its entirety.

FIELD OF THE INVENTION

The present invention relates to an iron- and copper-comprising heterogeneous catalyst, a process for producing it and a process for preparing olefins by reacting carbon monoxide with hydrogen in the presence of the iron- and copper-comprising heterogeneous catalyst.

BACKGROUND OF THE INVENTION

It is known that lower olefins can be prepared from carbon monoxide (CO) and hydrogen ($H_2$) over metal catalysts, e.g. iron or cobalt catalysts. Iron oxides are usually used as catalyst precursors. Such catalysts are described, for example, in U.S. Pat. No. 4,544,674, U.S. Pat. No. 5,100,856, U.S. Pat. No. 5,118,715, U.S. Pat. No. 5,248,701, US 2004/0127582 A1, H. P. Withers et al., Ind. Eng. Chem. Res. 1990, 29, pages 1807 to 1814, and M. E. Dry et al., Stud. Surf. Sci. Catal., Vol. 152, 2004, pages 533 to 600.

This reaction is also referred to as the Fischer-Tropsch synthesis.

Conventional processes for the Fischer-Tropsch synthesis produce hydrocarbons having a wide product distribution.

In principle, this range of the product distribution can be characterized by the Anderson-Schulz-Flory distribution; cf.: M. Janardanarao, Ind. Eng. Chem. Res. 1990, 29, pages 1735-53.

It is likewise known that the composition of the hydrocarbons formed in the Fischer-Tropsch process can be strongly influenced by the choice of catalysts used, the types of reactor and the reaction conditions.

For example, it is known that the product distribution can be shifted in the direction of lower olefins by use of high temperatures in the presence of modified iron catalysts: B. Büssemeier et al., Hydrocarbon Processing, November 1976, pages 105 to 112.

The main problem here is the formation of large amounts of undesirable methane ($CH_4$).

In addition, the iron oxides required as starting material for the catalyst are difficult to reduce.

DE 28 22 656 A1 (Inst. Fr. du Petrole) discloses a Fischer-Tropsch process in which the catalyst is obtained by precipitation of a metal-organic iron and/or cobalt and/or nickel aggregate on an inorganic support. The precipitation of the aggregate on the support is effected by impregnating the support with a solution of the aggregate. C2-C4-Olefins ("lower olefins") and only small amounts of methane are said to be formed selectively in this process. The main disadvantage of these catalysts is that the active catalyst constituents can be volatile under the reaction conditions, which results in a loss of metal, and that they are toxic.

DE 29 19 921 A1 (Vielstich et al.) describes a further Fischer-Tropsch process in which catalysts comprising polycrystalline iron whiskers as substantial catalyst component are used. These iron whiskers are obtained by thermal decomposition of iron pentacarbonyl in a magnetic field. The iron whiskers are preferably used as pellets. According to the teachings of this DE document, polycrystalline whiskers are fine iron threads having microscopically small single crystal regions (page 5, 3rd paragraph). The shape of the thread-like primary particles results from growth in the magnetic field. The threads have a length of, for example, from 0.06 to 1 mm.

The two figures in "Fachberichte für Oberflächentechnik", July/August 1970, page 146, show scanning electron micrographs of such a carbonyl iron powder having thread-like primary particles.

"Fachberichte für Oberflächentechnik", July/August 1970, pages 145 to 150, also describes these iron whiskers as metal hairs which result from crystal growth of the metal in thread form, unlike normal crystal growth (page 145, 2nd paragraph). In the polycrystalline iron whiskers, the ratio of length to diameter is, for example, ≥10.

Such polycrystalline iron whiskers are also described in H. G. F. Wilsdorf et al., Z. Metallkde. 69 (11), 1978, pages 701 to 705.

DE 25 07 647 A1 (Kölbel et al.) describes the use of catalysts comprising manganese and optionally iron for preparing hydrocarbons and oxygen-comprising compounds from CO and $H_2$.

U.S. Pat. No. 2,417,164 (Standard Oil Comp.) relates to processes for synthesizing liquid hydrocarbons from CO and $H_2$ in the presence of metal catalysts, including carbonyl iron powder.

WO 07/060,186 A1 (BASF AG) teaches processes for preparing olefins from synthesis gas using Fischer-Tropsch catalysts in a reaction column.

WO 09/013,174 A2 (BASF SE) relates to a process for preparing short-chain, gaseous olefins by reacting carbon monoxide with hydrogen in the presence of an iron-comprising heterogeneous catalyst, where carbonyl iron powder having spherical primary particles is used as catalyst.

Promoters in iron catalysts for Fischer-Tropsch syntheses are described, for example, in the abovementioned WO 09/013,174 A2 and in M. Janardanarao, Ind. Eng. Chem. Res. 1990, 29, pages 1735 to 1753, and C. D. Frohning et al. in "Chemierohstoffe aus Kohle", 1977, pages 219 to 299.

As suitable promoters, the catalyst can comprise, for example, one or more of the elements potassium, vanadium, copper, nickel, cobalt, manganese, chromium, zinc, silver, gold, calcium, sodium, lithium, cesium, platinum, palladium, ruthenium, sulfur, in each case in elemental form or in ionic form.

EP patent application no. 08164085.6 (BASF SE) of Sep. 10, 2008 describes an integrated process in which pure carbonyl iron powder (CIP) is prepared by decomposition of pure iron pentacarbonyl (IPC) in a plant A, in which carbon monoxide (CO) liberated in the decomposition of the IPC is used for preparing further CIP from iron in plant A or is fed to an associated plant B for preparing synthesis gas or is fed to an associated plant C for preparing hydrocarbons from synthesis gas and the CIP prepared in plant A is used as catalyst or catalyst component in an associated plant C for preparing hydrocarbons from synthesis gas from plant B.

Two parallel European patent applications having the same filing date (all BASF SE) relate to particular iron-comprising heterogeneous catalysts and their use in processes for preparing olefins by reacting carbon monoxide with hydrogen.

BRIEF SUMMARY OF THE INVENTION

It is an object of the present invention to overcome the disadvantages of the prior art and discover an improved catalyst and an improved economical process for preparing olefins. The process should, in particular, give lower olefins (e.g. C2-C6-olefins, in particular C2-C4-olefins), in particular ethene, propene and 1-butene, very selectively while at the same time forming very small amounts of methane, carbon dioxide, alkanes (e.g. C2-C6-alkanes, in particular C2-C4-alkanes) and higher hydrocarbons, i.e. hydrocarbons having, for example, seven or more carbon atoms (C7+ fraction), in particular five or more carbon atoms (C5+ fraction). Constituents of the catalyst should not be volatile under the reaction conditions.

Furthermore, the catalyst should have a shortened activation phase. The running-in time until the desired product spectrum is achieved, which is known for the Fischer-Tropsch synthesis, should be shortened.

The catalyst should have an improved operation life and increased mechanical stability. The increased stability is, in particular, advantageous when the catalyst is used in a fluidized bed or in slurry reactors or else in bubble columns.

According to the invention, the following aspects, inter alia, were recognized:

The metallic secondary particles formed with at least partial agglomeration in step II, particularly in a fluidizable fraction having particle diameters in the range 10-250 μm (see below), are ideal catalyst precursors for the synthesis of lower olefins from CO-rich synthesis gases because of their chemical composition. An additional advantage is the low surface area of the particles, which is preferably below 2 m$^2$/g (see below).

A particular advantage is the low oxygen content of the metallic secondary particles, as a result of which a reduction, and thus activation of the catalyst, is greatly simplified.

We have accordingly found an iron- and copper-comprising heterogeneous catalyst and a process for producing it, which comprises the following steps:

I. thermal decomposition of gaseous iron pentacarbonyl to give carbonyl iron powder having spherical primary particles, II. treatment of carbonyl iron powder obtained in step I with hydrogen, resulting in the metallic spherical primary particles at least partly agglomerating, III. surface oxidation of the iron particles from step II (i.e. agglomerates=secondary particles, and also any primary particles still present) to form iron oxide, IV. contacting of the particles from step III with an aqueous solution of a copper compound, V. drying in the presence of oxygen and subsequent calcination in the absence of oxygen, resulting firstly in oxygen-comprising copper compounds on the particles and finally reaction of these with the iron oxide to form a mixed oxide of the formula $Cu_xFe_{3-x}O_4$, where $0 < x \leq 1$.

Furthermore, we have accordingly found a process for preparing olefins by reacting carbon monoxide with hydrogen in the presence of a catalyst, wherein the abovementioned iron- and copper-comprising heterogeneous catalyst is used as catalyst.

The proportion of spherical primary particles in the carbonyl iron powder obtained in step I is preferably >90% by weight, particularly preferably >95% by weight, very particularly preferably >98% by weight.

The spherical primary particles obtained in step I preferably have a diameter in the range from 0.01 to 50 μm, particularly preferably in the range from 0.1 to 20 μm, very particularly preferably in the range from 0.5 to 15 μm, more particularly in the range from 0.7 to 10 μm, more particularly in the range from 1 to 10 μm.

The iron content of the spherical primary particles is preferably >97% by weight, particularly preferably ≥99% by weight, in particular ≥99.5% by weight.

The iron is preferably present in its most thermodynamically stable modification (alpha-iron).

The spherical primary particles are preferably free of pores.

In particular, the carbonyl iron powder has no thread-like primary particles in addition to the spherical primary particles, especially not the iron whiskers disclosed in DE-A1-29 19 921 and "Fachberichte für Oberflächentechnik", July/August 1970, pages 145 to 150 (see above).

Figure 1:
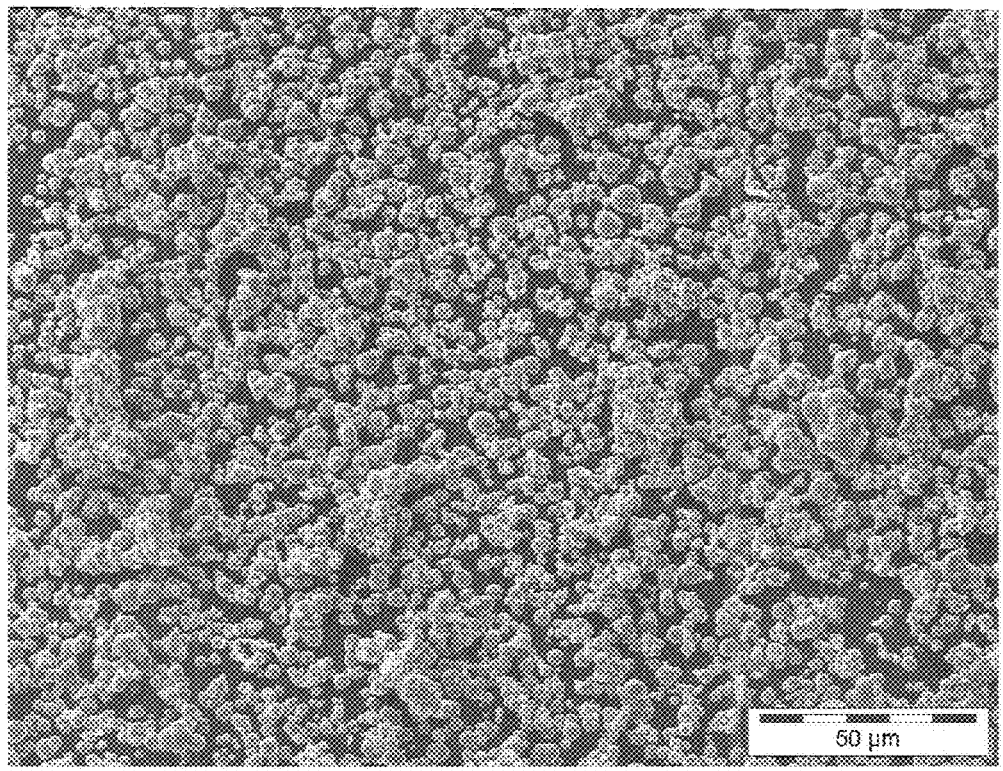
FIGS. 1-3 show scanning electron micrographs of preferred carbonyl iron powder having spherical primary particles before the hydrogen treatment according to step II in the disclosure.
Figure 2:
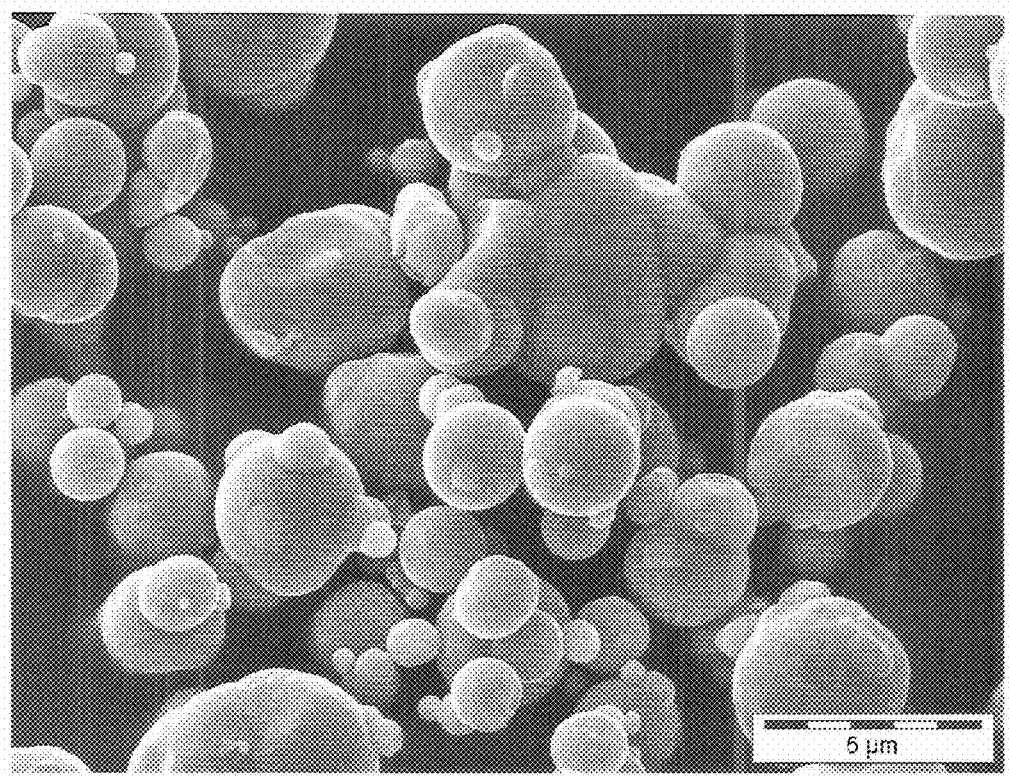
Figure 3:
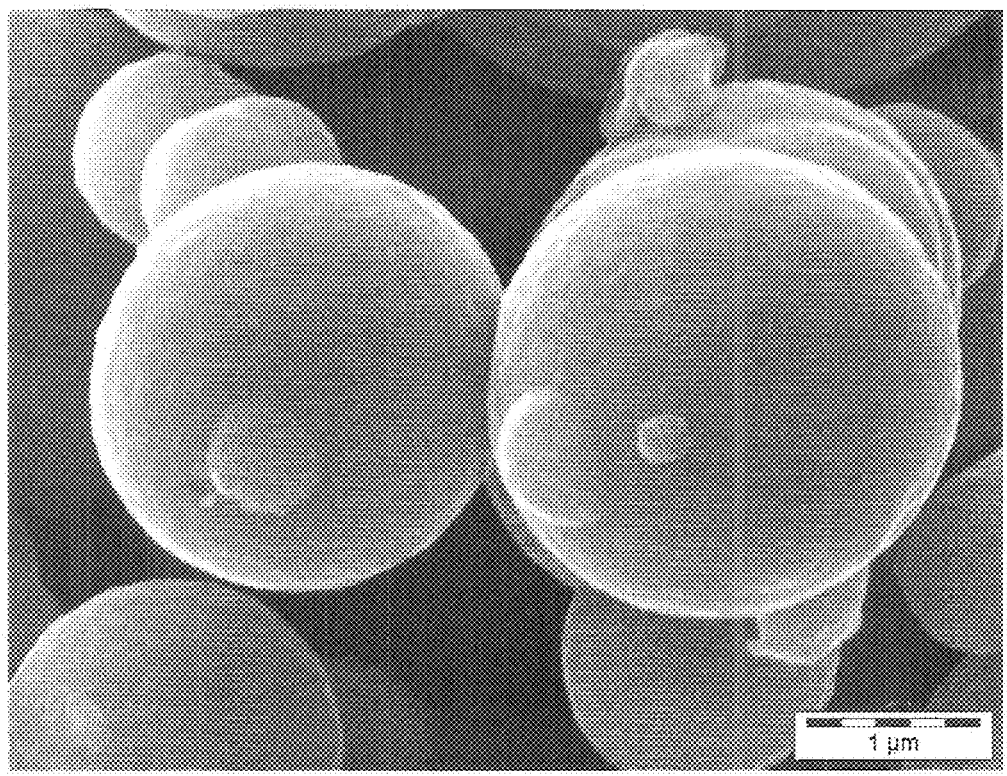

FIGS. 1 to 3 show scanning electron micrographs of preferred carbonyl iron powder having spherical primary particles before the hydrogen treatment according to step II.

Carbonyl iron powder having spherical primary particles which can be used in the process of the invention is, for example, obtainable under the trade name "carbonyl iron powder CN" from BASF AG or now BASF SE, D-67056 Ludwigshafen.

The carbonyl iron powder having spherical primary particles is obtained by thermal decomposition of gaseous iron pentacarbonyl ($Fe[CO]_5$), which has particularly preferably been purified beforehand by distillation.

The product obtained in step I is treated with hydrogen in step II. This treatment of the primary particles with hydrogen is preferably carried out at a temperature in the range from 300 to 600° C. This treatment lowers the residual content of carbon, nitrogen and oxygen in the CIP. (DE 528 463 C1, 1927). Here, the spherical primary particles are at least partly, e.g. to an extent of from 25 to 95% by weight, agglomerated.

The metallic secondary particles formed with at least partial agglomeration in step II preferably have particle diameters in the range from 10 to 250 μm, particularly preferably from 50 to 150 μm. Such fluidizable particle fractions can be obtained by appropriate sieving.

In step II, metallic secondary particles having BET surface areas (DIN ISO 9277) of preferably less than 2 m$^2$/g, in particular from 0.2 to 1.9 m$^2$/g, are formed.

Figure 4:
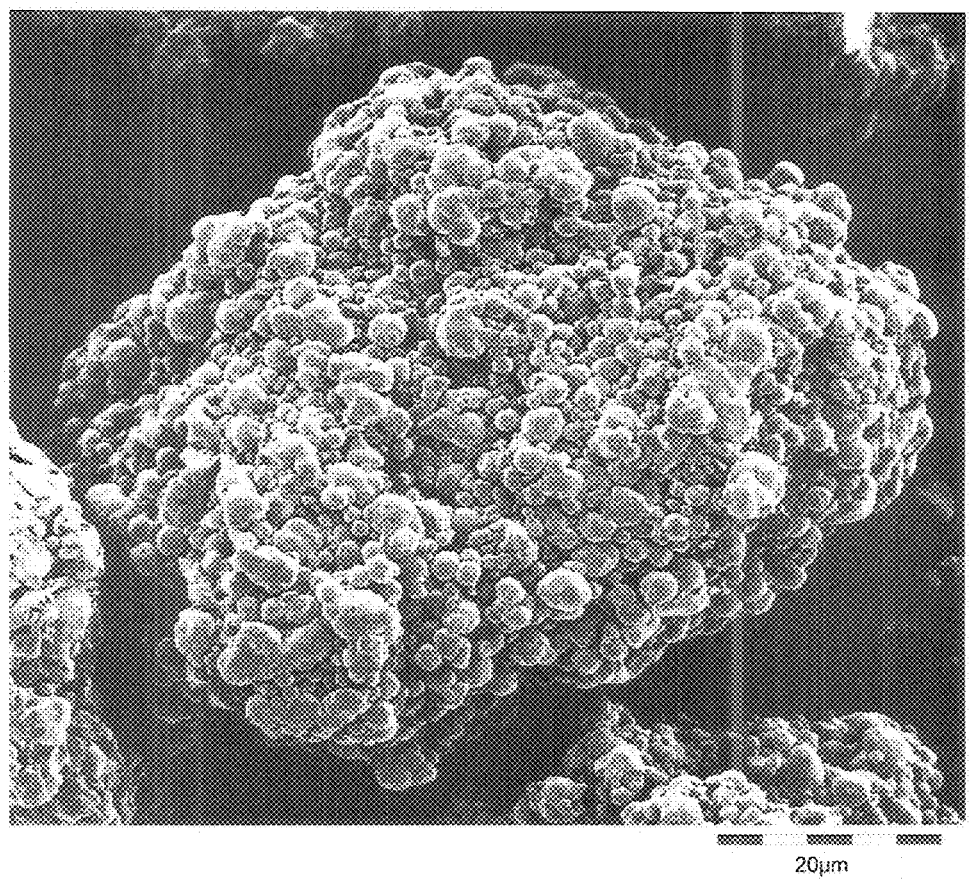
FIGS. 4-5 show, by way of example, agglomerates obtained after the hydrogen treatment.
Figure 5:
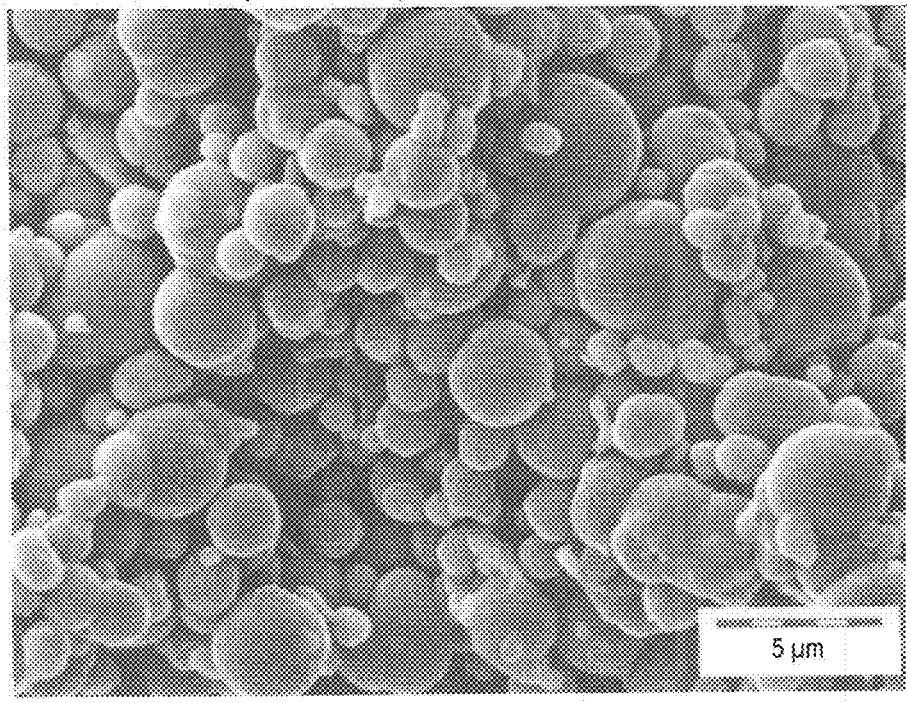
Figure 5:
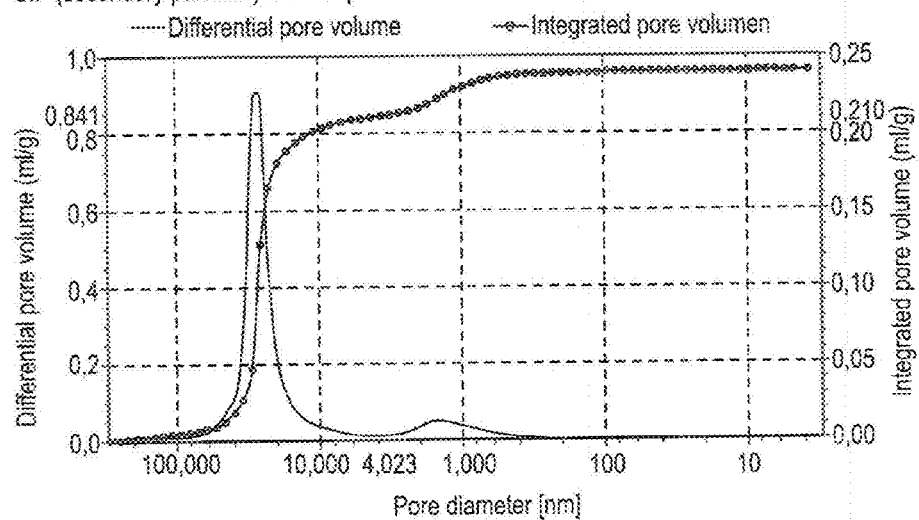

FIGS. 4 and 5 show, by way of example, agglomerates obtained after the hydrogen treatment.

In step III, the iron particles from step II (i.e. the agglomerates=secondary particles, and also any primary particles still present) are subjected to controlled surface oxidation (passivated). In this oxidation, iron oxide is formed on the surface of the particles. The oxidation, also referred to as passivation, is preferably carried out by means of oxygen. The oxygen can be used in the form of oxygen-comprising ($O_2$-comprising) water.

The oxidation is preferably carried out at temperatures below 150° C., particularly preferably at a temperature of less than 50° C., in particular at a temperature in the range from 20 to 45° C., e.g. in air diluted with inert gas, oxygen-comprising inert gas or by bringing the particles into contact with oxygen-comprising water, in this case preferably with stirring. Suitable inert gases are nitrogen or noble gases such as He, Ne, in particular argon.

In step IV, the surface-oxidized (passivated) particles are preferably brought into contact with an aqueous copper salt solution, in particular an aqueous solution of copper nitrate, copper carbonate or an organic copper salt; this is also referred to as impregnation or steeping.

In a particular embodiment, compounds which reduce the surface tension of the impregnation solution, e.g. surfactants, can be added to the aqueous copper salt solutions.

A particularly preferred copper salt is copper nitrate. Examples of organic copper salts are copper acetate, copper oxalate and copper acetylacetonate.

In step V, drying is carried out in the presence of oxygen, preferably in air, in particular at a temperature in the range from 50 to 150° C., preferably from 55 to 120° C.

Calcination in the absence of oxygen ($O_2$), preferably under inert gas (i.e. in an inert gas atmosphere), particularly preferably at a temperature in the range from 500 to 800° C., in particular from 600 to 750° C., is subsequently carried out. Suitable inert gases do not react with the iron and the dopants under the conditions and are, for example, noble gases such as He, Ne, in particular Ar.

Here, mixed oxides, in particular spinels, of the formula $Cu_xFe_{3-x}O_4$, where x is in the range from >0 to ≤1, in particular in the range from >0.25 to ≤1, are formed by reaction of the oxygen-comprising copper compounds formed with iron oxide.

The doping of the catalyst obtained in step V with Cu is preferably in the range from 0.5 to 4% by weight, particularly preferably from 0.6 to 2% by weight, very particularly preferably from 0.7 to 1.5% by weight, e.g. from 0.8 to 1.3% by weight, in each case based on iron and in each case calculated as element in the oxidation state 0.

In a particular variant, the particles are additionally doped with a total amount in the range from 0.01 to 1% by weight, particularly preferably from 0.05 to 0.5% by weight, (in each case based on iron and in each case calculated as element in the oxidation state 0) of alkaline metal ions and/or alkaline earth metal ions, in particular potassium ions and/or sodium ions.

This additional doping is, in particular, carried out after step V by contacting, more particularly in step V between drying and calcination by contacting, preferably in step IV by preferably simultaneous contacting of the particles (secondary particles and any primary particles still present) with an aqueous solution of an alkali metal compound and/or alkaline earth metal compound.

In a particular embodiment of the invention, steps IIa and IIb below are additionally carried out between steps II and III.

In step IIa, the agglomerates are preferably brought into contact with liquid or gaseous iron pentacarbonyl. Particular preference is given to liquid iron pentacarbonyl. For this purpose, the metal secondary particles are, for example, introduced into a vessel made inert by means of argon and dried at elevated temperature, e.g. from 70 to 150° C., in particular, for example, at an internal temperature of the vessel of 105° C. Iron pentacarbonyl is then introduced in liquid form in portions (e.g. of 5% by volume based on the amount of carbonyl iron powder), e.g. through an inlet tube.

The alternative contacting with gaseous iron pentacarbonyl can, for example, be carried out in a fluidized bed, in particular at a temperature in the range from 120 to 175° C. It is preferably carried out at an IPC partial pressure (absolute) in the range from 0.7 to 1 bar.

In step IIb, iron pentacarbonyl is thermally decomposed, preferably at a temperature in the range from 150 to 350° C., in particular in the range from 150 to 200° C. For example, the vessel in which the material from step III is present is heated to an internal temperature in the range of preferably from 150 to 180° C. and the decomposition reaction of the IPC applied is preferably monitored using an IR spectrometer. When the CO content of the offgas has passed its maximum, the vessel is cooled again to, for example, 105° C.

Depending on the desired degree of fill of the pores, the procedure of the two steps IIa and IIb is repeated.

Figure 7:
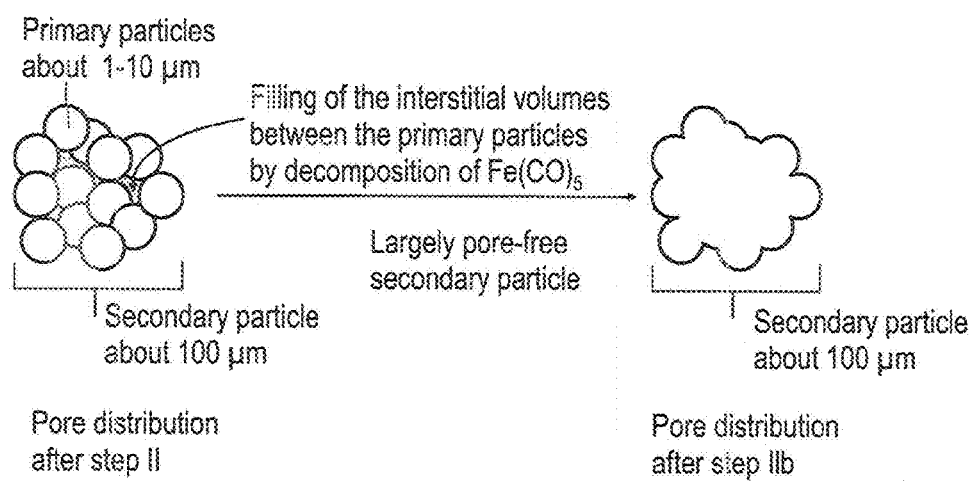
FIG. 7 show the pore distribution after step II and after step IIb.

Step IIb results in largely pore- and void-free secondary particles. The secondary particles obtained in step II comprise interstitial pores between the spherical primary particles (pore diameter, in particular, <4000 nm). The interstitial pores, in particular the interstitial pores having diameters of <4000 nm, thus represent intraparticulate pores (FIGS. 5 and 7), while the measured pores having diameters of, in particular, >4000 nm can be interpreted as interparticulate pores (resulting from the interstitial volume between the secondary particles).

The treatment of the secondary particles with iron pentacarbonyl makes it possible to fill the interstitial pores between the spherical primary particles, which have, in particular, pore diameters in the range of <4000 nm. This thus gives predominantly pore- and void-free secondary particles in which the differential pore volume for pore diameters in the range of <4000 nm is particularly preferably <10%, in a particular embodiment <5%, based on the measured integrated pore volume of the secondary particles.

The amount of iron pentacarbonyl necessary for filling the pores having a diameter of, in particular, <4000 nm is preferably determined by means of pore volume measurement by mercury porosimetry (DIN 66133).

Figure 6:
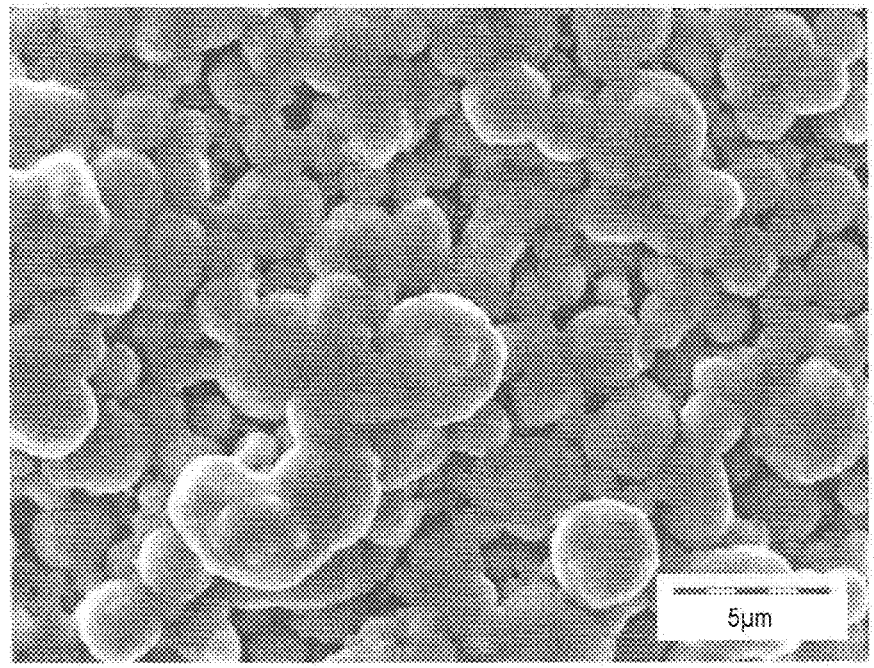
FIG. 6 shows a carbonyl iron powder filled by optional treatment with iron pentacarbonyl with a depiction of the pore structure.
Figure 6:
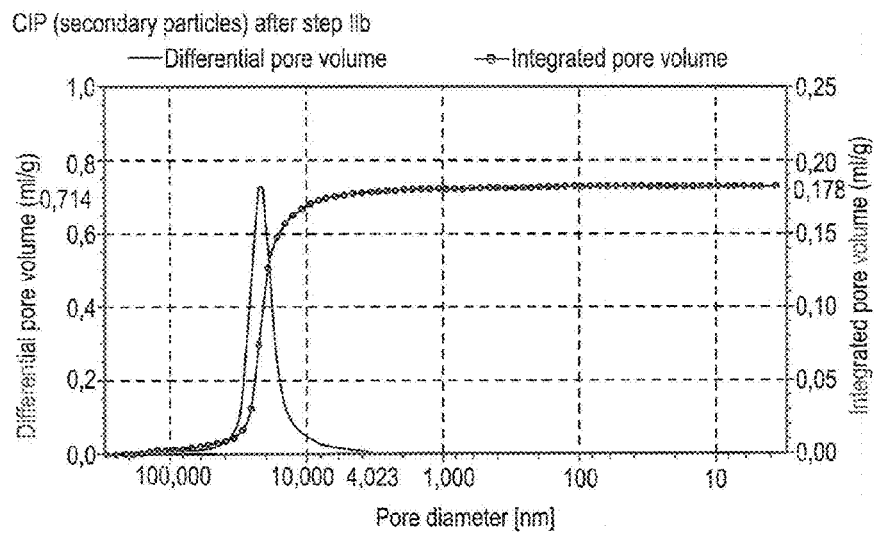

Particles obtained in step IIb are shown by way of example in FIG. 6.

The iron- and copper-comprising catalyst of the invention is particularly preferably not applied to a support material.

In the process of the invention, the optionally doped iron- and copper-comprising heterogeneous catalyst can be used in the form of pellets.

The pellets are obtained by methods known to those skilled in the art. Preferred forms of the pellets are tablets and rings.

The pellets can also be comminuted again, e.g. by milling, before use in the process of the invention.

The catalyst can be converted into a more synthesis-active state by treatment with hydrogen and/or carbon monoxide at elevated temperature, in particular at temperatures above 300° C., before being used in the process of the invention. However, this additional activation is not absolutely necessary.

In the process of the invention, the starting materials carbon monoxide and hydrogen are preferably used in the form of synthesis gas.

The synthesis gas can be produced by generally known processes (as described, for example, in Weissermel et al., Industrial Organic Chemistry, Wiley-VCH, Weinheim, 2003, pages 15 to 24), for example by reaction of carbon or methane with steam or by partial oxidation of methane. The synthesis gas preferably has a molar ratio of carbon monoxide to hydrogen in the range from 3:1 to 1:3. Particular preference is given to using a synthesis gas which has a molar mixing ratio of carbon monoxide to hydrogen in the range from 2:1 to 1:2.

In a particular embodiment of the process of the invention, the synthesis gas comprises carbon dioxide ($CO_2$). The content of $CO_2$ is preferably in the range from 1 to 50% by weight.

The process of the invention is preferably carried out at a temperature in the range from 200 to 500° C., in particular from 300 to 400° C.

The absolute pressure is preferably in the range from 1 to 100 bar, in particular from 5 to 50 bar.

The WHSV (weight hourly space velocity) is preferably in the range from 100 to 10 000, particularly preferably from 300 to 5000, parts by volume of feed stream per part by mass of catalyst and hour (l/kg·h).

Preferred reactors for carrying out the process of the invention are: fluidized-bed reactor, fixed-bed reactor, suspension reactor, microreactor.

In a fluidized-bed reactor, microreactor or suspension reactor, the catalyst is preferably used in powder form.

The powder can also be obtained by milling previously produced pellets.

In a fixed-bed reactor, the catalyst is used as shaped bodies, preferably in the form of pellets.

The use of such reactors for the Fischer-Tropsch synthesis is described, for example, in C. D. Frohning et al. in "Chemierohstoffe aus Kohle", 1977, pages 219 to 299, or B. H. Davis, Topics in Catalysis, 2005, 32 (3-4), pages 143 to 168.

The process of the invention gives a product mixture comprising olefins with an olefin-carbon selectivity, in particular an α-olefin-carbon selectivity, for the C2-C4 range of preferably at least 30%, e.g. in the range from 30 to 50%. In the selectivity indicated, carbon dioxide formed is not taken into account (i.e. excluding $CO_2$).

In a particular embodiment, a product mixture comprising olefins is obtained with an olefin-carbon selectivity for the C2-C4 range of at least 30%, e.g. in the range from 30 to 50%, with at least 90% of this at least 30% being in turn made up of ethene, propene, 1-butene. Carbon dioxide formed is not taken into account (i.e. excluding $CO_2$) in the selectivity indicated.

In a particularly preferred embodiment, a product mixture comprising olefins is obtained with an olefin-carbon selectivity for the C2-C4 range of at least 35%, e.g. in the range from 35 to 50%, with at least 90% of this at least 35% being in turn made up of ethene propene, 1-butene. Carbon dioxide formed is not taken into account (i.e. excluding $CO_2$) in the selectivity indicated.

The olefins obtained are used, for example, in processes for preparing polyolefins, epoxides, oxo products, acrylonitriles, acrolein, styrene. See also: Weissermel et al., Industrial Organic Chemistry, Wiley-VCH, Weinheim, 2003, pages 145 to 192 and 267 to 312.

All pressures indicated are absolute pressures.

EXAMPLES

Example 1

Comparative Catalyst

Production of K—/Cu-Doped Carbonyl Iron Catalyst by Impregnation 100 g of carbonyl iron material having a particle size distribution of the secondary particles such that 90% by weight have a diameter in the range from 50 to 100 μm, see FIG. 4, were prepared from carbonyl iron powder type CN, BASF AG or now BASF SE, by treatment with hydrogen at least 300° C. and impregnated under ambient conditions (room temperature, atmospheric pressure) with 11 ml of aqueous potassium nitrate/copper nitrate solution. The aqueous potassium nitrate/copper nitrate solution was produced by dissolving 3.87 g of copper nitrate (×2.5 $H_2O$, 99%, Riedel de Haen) and 0.66 g of potassium nitrate (99%, Riedel de Haen) in 11 ml of demineralized water. The impregnated catalyst was dried at 120° C. for 4 hours. The catalyst obtained comprised 0.23% by weight of K and 0.86% by weight of Cu.

Example 2

According to the Invention

Production of K—/Cu-Doped Carbonyl Iron Catalyst (Mixed Oxide) by Impregnation 150 g of carbonyl iron material having a particle size distribution of the secondary particles such that 90% by weight have a diameter in the range from 50 to 100 μm, see FIG. 4, were prepared from carbonyl iron powder type CN, BASF AG or now BASF SE, by treatment with hydrogen at least 300° C. and passivated in a controlled manner by means of 5% by volume of air in nitrogen in a rotary bulb oven at a temperature up to not more than 35° C. The surface-passivated carbonyl iron powder was impregnated under ambient conditions (room temperature, atmospheric pressure) with 16.5 ml of aqueous potassium nitrate/copper nitrate solution. The aqueous potassium nitrate/copper nitrate solution was produced by dissolving 5.56 g of copper nitrate (×2.5 $H_2O$, 99%, Riedel de Haen) and 0.79 g of potassium nitrate (99%, Riedel de Haen) in 16.5 ml of demineralized water. The impregnated catalyst was dried at 120° C. under a stream of air of 100 standard l/h for 4 hours in a rotary bulb oven. The catalyst is subsequently calcined at 650° C. under a stream of argon of 100 standard l/h for 10 hours.

The catalyst obtained comprised 0.17% by weight of K and 0.99% by weight of Cu.

Example 3

Filling of the Pores of Pure, Agglomerated Carbonyl Iron Powder (Secondary Particles) from Step II with Iron Pentacarbonyl According to Steps IIa and IIb.

The amount of iron pentacarbonyl necessary for filling the pores having a diameter of, in particular, <4000 nm was determined by means of mercury porosimetry (DIN 66133).

200 ml of carbonyl iron material having a particle size distribution of the secondary particles such that 90% by weight have a diameter in the range from 50 to 100 μm, see FIG. 4, were prepared from carbonyl iron powder type CN, BASF AG or now BASF SE, by treatment with hydrogen at least 300° C. The carbonyl iron material was dried at 105° C. under an argon atmosphere in a stirred vessel for 5 hours. 10 ml of iron pentacarbonyl were then introduced. The vessel was subsequently heated to an internal temperature of about 165° C. The decomposition occurred at 165° C. with stirring of the particles. The reaction was complete when no iron pentacarbonyl or no free carbon monoxide was detected in the offgas stream. These steps were repeated 13 times. After the synthesis was complete, the product was flushed with argon at 100° C. for at least 12 hours until the CO or $Fe(CO)_5$ content of the offgas was <0.1 ppm by volume.

Comparison:

Performance of the Catalyst According to the Invention (Example 2) and the Comparative Catalyst (Example 1) in the Process of the Invention with Prior Identical Activation A series of comparative performance tests using in each case about 2.0 g of catalyst (examples 1, 2; WHSV=500 standard l/kg·h) and dilution with inert material (catalyst:

silicon carbide=1:3 (weight ratio)) was carried out. The catalysts were introduced into a fixed-bed reactor and preactivated in $H_2:N_2$ (9:1) (molar) at 380° C. for 4 hours. Synthesis gas was then introduced into the reactor at a rate of about 0.9 standard l/h at 25 bar and the temperature was reduced to 340° C. As internal standard for later analytical tests, 0.1 standard l/h of nitrogen gas was additionally introduced. The results of the experiments carried out over a period of at least 75 hours are shown below for the respective catalyst systems.

(Standard l=standard liters=volume converted to S.T.P., WHSV=weight hourly space velocity).

| Catalyst | Example 1 | Example 2 (according to the invention) |
|---|---|---|
| Synthesis gas ratio $H_2/CO$ | 0.91 | 0.91 |
| WHSV [standard l/kg · h] | 500 | 500 |
| % CO conversion | 97.5 | 96.1 |
| % carbon selectivity to $CH_4$, without $CO_2$ | 10.9 | 7.8 |
| % carbon selectivity to C2-C4-olefins, without $CO_2$ | 24.8 | 35.6 |
| % carbon C7+, without $CO_2$ | 40.9 | 27.2 |

Carbon dioxide formed is not taken into account (i.e. without $CO_2$) in the selectivities indicated in the examples.

It can be seen that according to the invention methane formation is reduced and at the same time the yield of C2-C4-olefins is increased.

Analysis of the Reaction Products:

The product streams were sampled via heated stream selectors and lines after the long-chain hydrocarbons had been condensed out in a hot separator (about 160° C., 25 bar), and fed to an on-line gas chromatograph (GC).

GC: Agilent 6890N with FID and TCD.

Precolumns: CP-Poraplot Q, length 12.5 m, ID 0.53 mm, film thickness 20 μm

FID:

Injector 250° C., split ratio 50:1, carrier gas helium, column Durabond DB-1 (length 60 m, ID 0.32 mm, film thickness 3 μm), detector 280° C.

TCD:

Injector 200° C., split ratio 10:1, carrier gas argon, column Carboxen 1010 (length 30 m, ID 0.53 mm), detector 210° C.

Temperature program: 40° C.-5 min-7° C./min-250° C.-5 min, carrier gas helium.

FIGS. 1 to 3 below:

Carbonyl iron powder (CIP) having spherical primary particles which can be used according to the invention in step II.

The invention claimed is:

1. A process for producing an iron- and copper-comprising heterogeneous catalyst, which comprises the following steps:
   I. thermal decomposition of gaseous iron pentacarbonyl to give carbonyl iron powder having spherical primary particles,
   II. treatment of carbonyl iron powder obtained in step I with hydrogen, resulting in the metallic spherical primary particles at least partly agglomerating,
   III. surface oxidation of the iron particles from step II (agglomerates=secondary particles, and also any primary particles still present) to form iron oxide,
   IV. contacting of the particles from step III with an aqueous solution of a copper compound,
   V. drying in the presence of oxygen and subsequent calcination in the absence of oxygen, resulting firstly in oxygen-comprising copper compounds on the particles and finally reaction of these with the iron oxide to form a mixed oxide of the formula $Cu_xFe_{3-x}O_4$, where $0<x\leq1$.

2. The process according to claim 1, wherein the oxidation in step III is carried out by means of oxygen.

3. The process according to claim 1, wherein the particles are brought into contact with an aqueous copper salt solution in step IV.

4. The process according to claim 3, wherein the copper salt is copper nitrate or copper carbonate.

5. The process according to claim 1, wherein the drying of the particles in step V is carried out at a temperature in the range from 50 to 150° C. and the calcination of the particles is carried out at a temperature in the range from 500 to 800° C.

6. The process according to claim 1, wherein the spherical primary particles obtained in step I have a diameter in the range from 0.01 to 50 μm.

7. The process according to claim 1, wherein the secondary particles (=agglomerates) used in step III have a diameter in the range from 10 to 250 μM.

8. The process according to claim 1, wherein the primary particles obtained in step I have an iron content of greater than 97% by weight.

9. The process according to claim 1, wherein the primary particles obtained in step I are pore-free.

10. The process according to claim 1, wherein the carbonyl iron powder obtained in step I comprises no thread-like primary particles.

11. The process according to claim 1, wherein the total doping of the catalyst obtained in step V with Cu is in the range from 0.5 to 4% by weight (based on iron).

12. The process according to claim 1, wherein the particles are additionally doped with a total amount in the range from 0.01 to 1% by weight (based on iron) of alkali metal ions and/or alkaline earth metal ions.

13. The process according to claim 12, wherein the doping in step IV is effected by bringing the particles (secondary particles and any primary particles still present) into contact with an aqueous solution of an alkali metal compound and/or alkaline earth metal compound.

14. The process according to claim 1, wherein the particles are additionally doped with a total amount in the range from 0.01 to 1% by weight (based on iron) of potassium ions and/or sodium ions.

15. The process according to claim 1, which additionally comprises, between steps II and III, steps IIa and IIb below:
   IIa. contacting of the agglomerates (=secondary particles) with iron pentacarbonyl,
   IIb. thermal decomposition of the iron pentacarbonyl applied in step III to give at least predominantly pore- and void-free secondary particles.

16. The process according to claim 15, wherein the agglomerates are brought into contact with liquid or gaseous iron pentacarbonyl in step IIa.

17. The process according to claim 15, wherein the thermal decomposition of the iron pentacarbonyl in step IIb is carried out at a temperature in the range from 150 to 350° C.

18. An iron- and copper-comprising heterogeneous catalyst obtained by the process according to claim 1, wherein the at least partly agglomerating metallic spherical primary particles of step II agglomerate to form metallic secondary particles having BET surface areas of less than 2 $m^2/g$, and wherein the drying in the presence of oxygen of step V takes place at a temperature of from 50° C. to 150° C.

19. A process for preparing olefins by reacting carbon monoxide with hydrogen in the presence of a catalyst, wherein the iron- and copper-comprising heterogeneous catalyst according to claim 18 is used as catalyst.

20. The process according to claim 19, wherein the reaction is carried out at a temperature in the range from 200 to 500° C.

21. The process according to claim 19, wherein the reaction is carried out at an absolute pressure in the range from 1 to 100 bar.

22. The process according to claim 19 for preparing C2-C4-olefins.

23. The process according to claim 19, wherein carbon monoxide and hydrogen are used in the form of synthesis gas for the reaction.

24. The process according to claim 23, wherein the synthesis gas comprises carbon dioxide ($CO_2$).

25. The process according to claim 19, wherein carbon monoxide and hydrogen are used in a molar ratio in the range from 2:1 to 1:2.

* * * * *